United States Patent
Ke et al.

(10) Patent No.: US 8,513,308 B2
(45) Date of Patent: Aug. 20, 2013

(54) PAK1 AGONISTS AND METHODS OF USE

(75) Inventors: Yunbo Ke, Chicago, IL (US); Ross John Solaro, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 243 days.

(21) Appl. No.: 13/057,929

(22) PCT Filed: Aug. 7, 2009

(86) PCT No.: PCT/US2009/053154
§ 371 (c)(1),
(2), (4) Date: Feb. 7, 2011

(87) PCT Pub. No.: WO2010/017478
PCT Pub. Date: Feb. 11, 2010

(65) Prior Publication Data
US 2011/0152221 A1    Jun. 23, 2011

Related U.S. Application Data

(60) Provisional application No. 61/087,519, filed on Aug. 8, 2008, provisional application No. 61/138,250, filed on Feb. 4, 2009, provisional application No. 61/151,095, filed on Feb. 9, 2009.

(51) Int. Cl.
*A61K 31/135*   (2006.01)

(52) U.S. Cl.
USPC .................................................. 514/647

(58) Field of Classification Search
USPC ........................................................ 514/647
See application file for complete search history.

(56) References Cited

U.S. PATENT DOCUMENTS

| | | |
|---|---|---|
| 2002/0086390 A1 | 7/2002 | Traugh et al. |
| 2003/0027304 A1* | 2/2003 | Sabbadini ................ 435/184 |
| 2003/0153009 A1 | 8/2003 | He et al. |
| 2004/0102623 A1 | 5/2004 | Monia et al. |

FOREIGN PATENT DOCUMENTS

WO   WO-2005/011721 A2   2/2005

OTHER PUBLICATIONS

Argraves et al., Sphingolipids in vascular biology, *Adv. Exp. Med. Biol.*, 507: 439-44 (2002).
Bagheri-Yarmand et al., Etk/Bmx tyrosine kinase activates Pak1 and regulates tumorigenicity of breast cancer cells, *J. Biol. Chem.* 276: 29403-9 (2001).
Bokoch et al., A GTPase-independent mechanism of p21-activated kinase activation. Regulation by sphingosine and other biologically active lipids, *J. Biol. Chem.*, 273: 8137-44 (1998).
Chik et al., Ceramide inhibits L-type calcium channel currents in GH3 cells, *Mol. Cell Endocrinol.*, 218: 175-83 (2004).
Chik et al., Ceramide inhibits L-type calcium channel currents in rat pinealocytes, *Endocrinology*, 140: 5682-90 (1999).
Chong et al., The mechanism of PAK activation. Autophosphorylation events in both regulatory and kinase domains control activity, *J. Biol. Chem.*, 276: 17347-53 (2001).
Dobrowsky et al., Ceramide activates heterotrimeric protein phosphatase 2A, *J. Biol. Chem.*, 268: 15523-30 (1993).

(Continued)

*Primary Examiner* — San-Ming Hui
(74) *Attorney, Agent, or Firm* — Marshall, Gerstein & Borun LLP

(57) ABSTRACT

The present invention is directed to Pak1 agonists and methods of use.

20 Claims, 6 Drawing Sheets

Purification of endogenous Pak1 from cardiac muscle

(56) References Cited

OTHER PUBLICATIONS

Furuya et al., Cell permeable exogenous ceramide reduces infarct size in spontaneously hypertensive rats supporting in vitro studies that have implicated ceramide in induction of tolerance to ischemia, *J. Cereb. Blood Flow Metab.*, 21: 226-32 (2001).

He et al., The Tyr-kinase inhibitor AG879, that blocks the ETK-PAK1 interaction, suppresses the RAS-induced PAK1 activation and malignant transformation, *Cancer Biol. Ther.*, 3:96-101 (2004).

Ke et al., Inhibition of endothelial barrier dysfunction by P21-activated kinase-1, *Can. J. Physiol. Pharmacol.* 85: 281-8 (2007).

Ke et al., Intracellular localization and functional effects of P21-activated kinase-1 (Pak1) in cardiac myocytes, *Circ. Res.*, 94: 194-200 (2004).

Ke et al., Regulation of L-type calcium channel and delayed rectifier potassium channel activity by p21-activated kinase-1 in guinea pig sinoatrial node pacemaker cells, *Circ. Res.*, 100: 1317-27 (2007).

Ke et al., Use of a decoy peptide to purify p21 activated kinase-I in cardiac muscle and identification of ceramide-related activation, *Biologics*, 2(4): 903-9 (2008).

Latimer et al., Bronchconstriction of the asthmatic airway by inhaled and ingested propranolol, *Eur. J. Pharmacol.*, 39: 441-5 (1990).

Lecour et al., Ceramide-induced preconditioning involves reactive oxygen species, *Life Sci.*, 78: 1702-6, (2006).

Lei et al., Structure of PAK1 in an autoinhibited conformation reveals a multistage activation switch, *Cell*, 102: 387-97 (2000).

Manser et al., Expression of constitutively active alpha-Pak reveals effects of the kinase on actin and focal complexes, *Mol. Cell Biol.*, 17: 1129-43 (1997).

Nagy et al., Bronchial obstruction exacerbated during β blocker therapy, *Orv. Hetil.*, 130: 2365-8 (1989). Abstract Only.

O'Byrne et al., Lack of costimulation by both sphingomyelinase and C2 ceramide in resting human T cells, *Immunology*, 100: 225-30 (2000).

Pirruccello et al., A dimeric kinase assembly underlying autophosphorylation in the p21 activated kinases, *J. Mol. Biol.*, 361: 312-26 (2006).

Polverino et al., Activation of mitogen-activated protein kinase cascades by p21-activated protein kinases in cell-free extracts of *Xenopus oocytes*, *.J Biol. Chem.*, 270: 26067-70 (1995).

Roig et al., Cdc42-independent activation and translocation of the cytostatic p21-activated protein kinase gamma-PAK by sphingosine, *FEBS Lett.*, 507: 195-9 (2001).

Ruvolo et al., Ceramide induces Bcl2 dephosphorylation via a mechanism involving mitochondrial PP2A, *J. Biol. Chem.*, 274: 20296-300 (1999).

Sheehan et al., p21-Activated kinase-1 and its role in integrated regulation of cardiac contractility, *Am. J. Physiol. Regul. Integr. Comp. Physiol.*, 293: R963-73 (2007).

Shin et al., β-Blocker pharmacogenetics in heart failure, *Heart Fail. Rev.*, 15(3): 187-96 (2008).

Sussman et al., Altered focal adhesion regulation correlates with cardiomyopathy in mice expressing constitutively active rac1, *J. Clin. Invest.*, 105: 875-86 (2000).

Thullberg et al., The kinase-inhibitory domain of p21-activated kinase 1 (PAK1) inhibits cell cycle progression independent of PAK1 kinase activity, *Oncogene*, 26: 1820-8 (2007).

Tsakiridis et al., Insulin activates a p21-activated kinase in muscle cells via phosphatidylinositol 3-kinase, *J. Biol. Chem.* 271: 19664-7 (1996).

Yang et al., The epidermal growth factor receptor tyrosine kinase inhibitor ZD1839 (Iressa) suppresses c-Src and Pak1 pathways and invasiveness of human cancer cells, *Clin. Cancer Res.*, 10: 658-67 (2004).

Zenke et al., Identification of a central phosphorylation site in p21-activated kinase regulating autoinhibition and kinase activity, *J. Biol. Chem.*, 274: 32565-73 (1999).

Zhao et al., A conserved negative regulatory region in alphaPAK: inhibition of PAK kinases reveals their morphological roles downstream of Cdc42 and Rac1, *Mol. Cell Biol.*, 18: 2153-63 (1998).

Zhao et al., Interaction between PAK and nck: a template for Nck targets and role of PAK autophosphorylation, *Mol. Cell Biol.*, 20: 3906-17 (2000).

Zhao et al., PAK and other Rho-associated kinases—effectors with surprisingly diverse mechanisms of regulation, *Biochem. J.*, 386: 201-14 (2005).

International Search Report and Written Opinion of the International Searching Authority, Korean Intellectual Property Office, PCT/US2009/053154, dated Mar. 15, 2010.

International Preliminary Report on Patentability, PCT/US2009/053154, dated Feb. 8, 2011.

\* cited by examiner

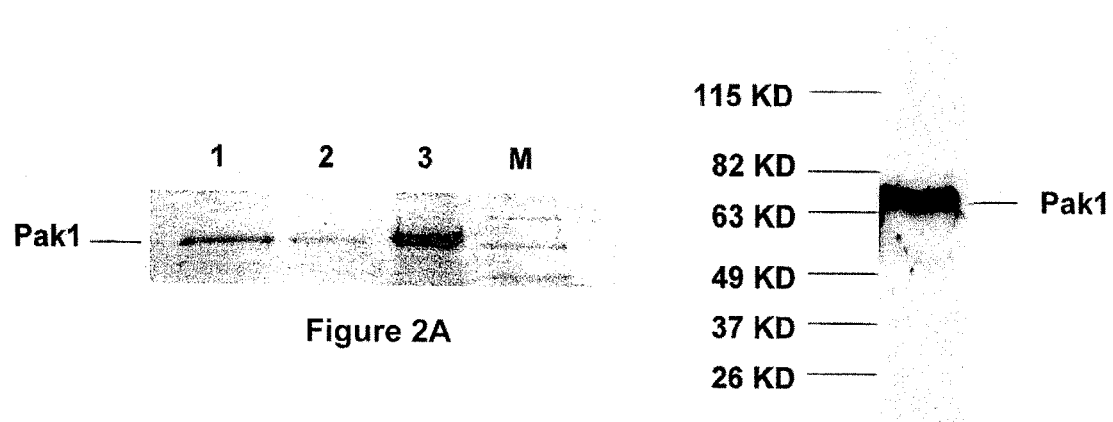
Figure 2A
Figure 2B
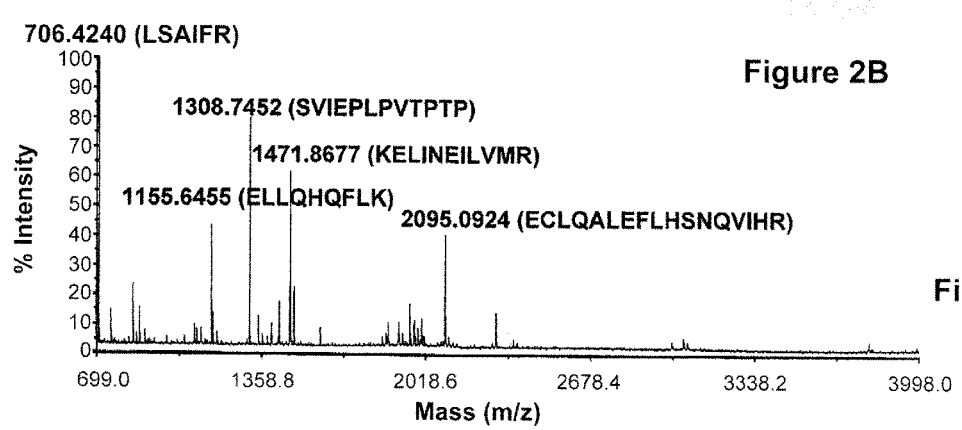
Figure 2C

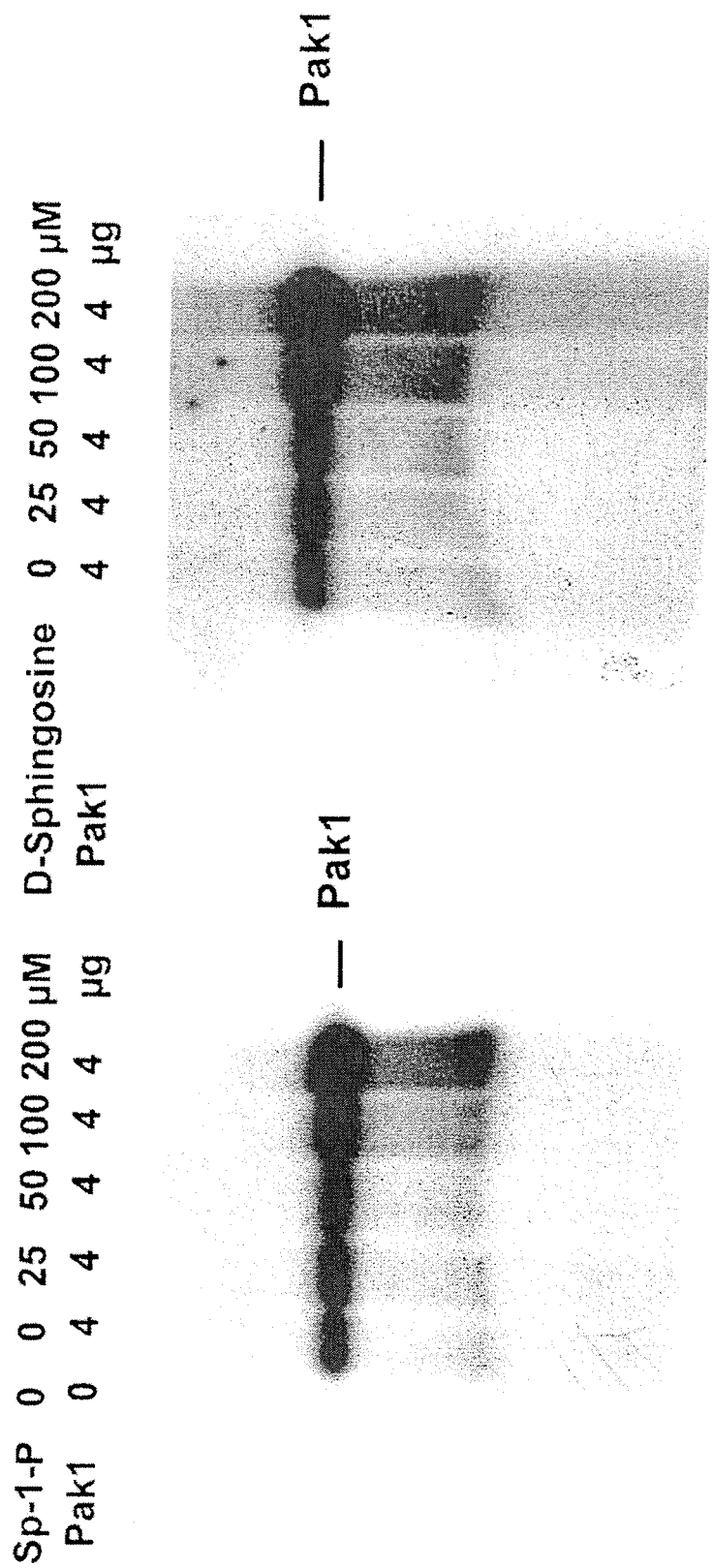

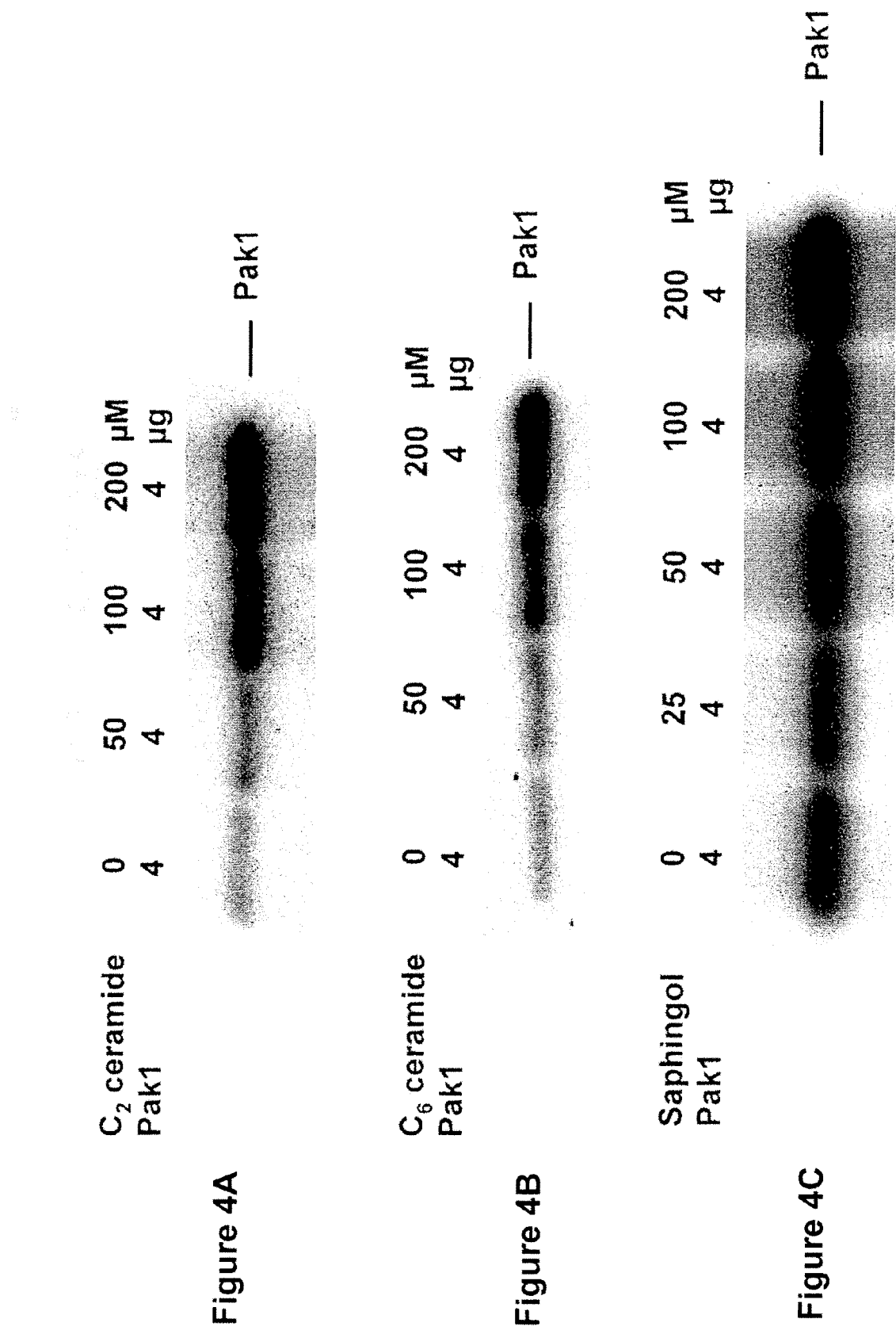

PAK1 AGONISTS AND METHODS OF USE

CROSS-REFERENCE TO RELATED APPLICATIONS

The present application claims the benefit of priority based on U.S. Provisional Application Nos. 61/087,519, 61/138,250 and 61/151,095 filed Aug. 8, 2008, Feb. 4, 2009, and Feb. 9, 2009, respectively. The disclosure of each priority application is incorporated herein by reference in its entirety.

GOVERNMENT INTEREST

This invention was made with U.S. government support under grant nos. HL64035 and HL22231, awarded by the National Institutes of Health. The U.S. government has certain rights in the invention.

BACKGROUND OF THE INVENTION

The $p^{21}$ activated kinase-1 (Pak1) belongs to a family of serine/threonine protein kinases directly activated by small GTPases, Cdc42 and Rac1. Pak1 is abundant in the heart and localizes to cell and nuclear membranes, intercalated discs and to Z-discs in ventricular myocytes. The active form of Pak1 in cardiomyocytes increases Ca2+ sensitivity of myofilament force development through activation of PP2A (Ke 2004, p 194-200) and in SA nodal cells, Pak1 inhibits isoproterenol-stimulated activation of L-type Ca2+ channel and delayed rectifier potassium channels (Ke 2007, p 1317-1327). Other studies have shown that in endothelial cells, Pak1 activation induces dephosphorylation of myosin regulatory light chain and inhibition of thrombin-induced barrier dysfunction (Ke 2007, p 281-288) and in HeLa cells, expression of constitutively active Pak1 induces loss of stress fibers and dissolution of focal adhesion complexes (Manser 1997, p 1129-1143). These studies suggest a role of Pak1 in cytoskeletal function and reorganization. In transgenic mice expressing an active Rac1 in the heart, hypertrophy developed followed by dilated cardiomyopathy with altered intracellular partitioning of Pak1 in the ventricle myocytes (Sussman 2000, p 875-886).

A prominent post-translational modification of Pak1 is autophosphorylation, which is correlated with its activity (Manser 1997, p 1129-1143; Zhao 1998, p 2153-2163). Pak1 is autophosphorylated at seven serine/threonine sites most of which occur at the N-terminal half of the kinase. Substitution of threonine 423, the last autophosphorylation site, with glutamic acid renders the kinase constitutively active (Manser 1997, p 1129-1143). Although there is abundant expression of Pak1 in cardiomyocytes, smooth muscle and endothelial cells, the function of Pak1 in the cardiovascular system remains poorly understood (Sheehan 2007, p 963-973). Moreover, potential modifications in autophosphorylation of native Pak1 in failing heart and in other pathological conditions have not been defined.

Studies in skeletal muscle have shown that Pak1 activity was responsive to insulin treatment (Tsakiridis 1996, p 19664-19667) suggesting that Paks are also phosphorylated by tyrosine kinase (Bagheri-Yarmand 2001, p 29403-29409; He 2004, p 96-101; Yang 2004, p 658-667). Tyrosine phosphorylation of Pak1 may also play an important role in regulation of cardiac function.

SUMMARY OF THE INVENTION

In one embodiment, the invention provides a method of treating a cardiac disorder in a mammalian subject comprising administering to the subject a Pak1 agonist in amount effective to treat the disorder. Also provided is a method of treating a cardiac disorder in a subject in which treatment with a standard of care therapeutic is contraindicated, wherein the method comprises administering to the subject a Pak1 agonist in amount effective to treat the disorder. In the context of methods of the invention, "standard of care" refers to a treatment that is generally accepted by clinicians for a certain type of patient diagnosed with a type of illness. In one embodiment, the contraindicated standard of care therapeutic is a β-blocker.

Exemplary cardiac disorders include, but are not limited to systolic heart failure, ischemia, arrhythmias, atrial fibrillation, atherosclerosis and angina pectoris. In some embodiments, the Pak1 agonist is a sphingolipid or analog thereof. In one embodiment, the Pak1 agonist is selected from the group consisting of a ceramide (including, but not limited to C2-ceramide and C6-ceramide), safingol, D-sphingosine and sphingosine 1-phosphate and molecules structurally related to C2/C6 ceramide and demonstrate the same functional effects in cardiac cells as the active Pak1 does including inhibition of heart rate (pacemaking activity), such as fingolimod (FTY720) and FTY720 derivatives that contains one or more unsaturated carbon bonds in its hydrophobic side chain.

Some embodiments of the methods described herein further comprise administering a standard of care therapeutic to the subject. For cardiac disorders, for example, an aspect of the invention is to improve standard of care therapy with co-therapy by administering one or more Pak1 agonists described herein. Exemplary standard of care therapeutics include, but are not limited to, β-blockers (if not contraindicated), nitrates and calcium-channel blockers. In one embodiment, the Pak1 agonist and the standard of care therapeutic are administered concurrently (e.g., in either a single formulation or separate formulations). In another embodiment, the Pak1 agonist and the standard of care therapeutic are administered sequentially.

In some embodiments, the subject is human. In one embodiment, the human is asthmatic.

Methods of identifying a Pak1 agonist are also provided. The method comprises contacting a candidate compound with purified Pak1, wherein a compound that enhances autophosphorylation of Pak1 compared to Pak1 autophosphorylation in the absence of the compound is identified as a Pak1 agonist. Another embodiment of the invention includes the identification of Pak1 antagonists. For example, the invention provides a method of identifying a Pak1 antagonist comprising contacting a candidate compound with purified Pak1 in the presence of a Pak1 agonist, wherein a compound that inhibits autophosphorylation of Pak1 in the presence of the agonist compared to Pak1 autophosphorylation in the absence of the compound is identified as a Pak1 antagonist. Exemplary candidate compounds include, but are not limited to, a nucleic acid, a polypeptide or fragment thereof, an antibody or antigen-binding fragment thereof, and a small molecule.

In some embodiments, the contacting step of the method is performed in a reaction mixture that includes a radioactive phosphorous reagent (including, but not limited to, ($^{32}$P gamma ATP), and phosphorylation is determined by detecting a radioactive phosphorous attached to the purified Pak1 polypeptide.

In some embodiments, the methods comprise purifying the Pak1 polypeptide from a cardiac sample. In one embodiment, the purified Pak1 is isolated from a heart muscle homogenate with a decoy Pak1 peptide. In some embodiments, the decoy Pak1 peptide comprises a portion of a Pak1 sequence linked to a heterologous peptide (including, but not limited to an hemagglutinin (HA) epitope).

In some embodiments, the decoy Pak1 peptide comprises amino acids 131-150 of the human Pak1 polypeptide sequence set forth in SEQ ID NO: 1. In one embodiment, the decoy Pak1 peptide comprises YNSKKTSNSQKYMSFT-DKSAYPYDVPDYA (SEQ ID NO: 3). In another embodiment, the decoy Pak1 peptide comprises MSNNGLDIQDK-PPAPPMRNTSTYPYDVPDYA (SEQ ID NO: 4).

Other aspects of the invention include use of a Pak1 agonist described herein in the manufacture of a medicament for the treatment of a cardiac disorder. In some embodiments, the medicament is for the treatment of a cardiac disorder where treatment with a standard of care therapeutic is contraindicated. In one embodiment, the medicament is for the treatment of a cardiac disorder selected from the group consisting of systolic heart failure, ischemia, arrhythmias, atrial fibrillation, atherosclerosis and angina pectoris.

This document is intended to be related as a unified disclosure, and it should be understood that all combinations of features described herein are contemplated, even if the combination of features are not found together in the same sentence, or paragraph, or section of this document.

BRIEF DESCRIPTION OF THE FIGURES

FIG. 2A is a picture of a gel demonstrating the purity of Pak1 at various stages of the affinity chromatography method described in Example 1. Lane 1: Cardiac muscle extracts resolved on a SDS page. Lane 2: The cardiac muscle extract after fractionation by 25% and 50% (NH4)2SO4 precipitation. Lane 3: Pak1 purified from the fractionated muscle sample. Lane M: The molecular weight markers.

FIG. 2B shows the detection of purified Pak1 by Western blotting analysis. Pak1 was detected as a single band with an antibody from Santa CruZ (sc-881).

FIG. 2C shows purified Pak1 detected by mass spectrometry. Peaks match the Pak1 peptides produced by theoretical trypsin digestion. The positions of amino acids of each peptide from Pak1 were denoted in quotation: LSAIFR (amino acids 490-495 of SEQ ID NO: 1), ELLQHQFLK (amino acids 514-522 of SEQ ID NO: 1), SVIEPLPVTPTR (amino acids 204-215 of SEQ ID NO: 1), KELIINEILVMR (amino acids 309-320 of SEQ ID NO: 1), ECLQALEFLHSNQVIHR (amino acids 372-388 of SEQ ID NO: 1).

FIG. 3A demonstrates that autophosphorylation of Pak1 is stimulated by sphingosine-phosphate in vitro.

FIG. 3B demonstrates that autophosphorylation of Pak1 is stimulated by D-erythro-sphingosine in vitro.

FIGS. 4A-4C demonstrate that autophosphorylation of Pak1 is stimulated by C2-ceramide, C6-ceramide and saphingol, respectively, in vitro.

DETAILED DESCRIPTION

Figure 1B:
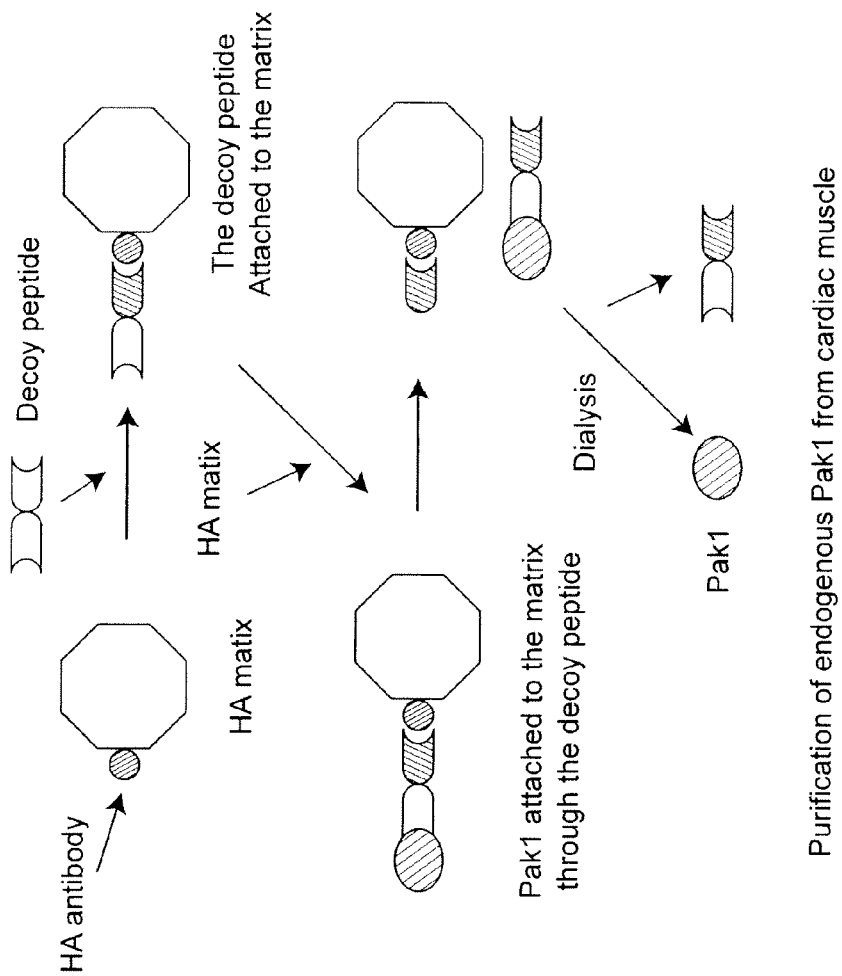
FIG. 1B is a schematic representation of purification of Pak1 from cardiac muscle.

The present invention is based on the discovery that compounds that stimulate or enhance of Pak1 autophosphorylation can be used for the treatment of various cardiac disorders.

I. Screening Assays for Modulators of Pak1 Autophosphorylation

One aspect of the present invention is directed to methods of identifying compounds that modulate Pak1 autophosphorylation. Such methods provide lead compounds and therapeutics for modulating Pak1 activity and cellular responses that are influenced by Pak1. Generally, such methods involve introducing one or more candidate compounds (alone or simultaneously) into a controlled system containing a purified Pak1 polypeptide, to determine whether the candidate compound modulates the autophosphorylation of Pak1.

To identify a candidate compound as being capable of modulating (stimulating/enhancing or inhibiting/decreasing) Pak1 autophosphorylation, one measures Pak1 autophosphorylation in the absence of the added candidate compound. A candidate agonist/antagonist compound is then contacted with Pak1 and the autophosphorylation (or lack thereof) of Pak1 is determined in the presence of the candidate agonist/antagonist compound. A candidate antagonist compound would decrease or inhibit Pak1 autophosphorylation, relative to the same parameter in its absence, whereas a candidate agonist will increase or stimulate Pak1 autophosphorylation, relative to the parameter in its absence.

In one aspect, the invention provides methods of identifying a Pak1 agonist comprising contacting a candidate compound with purified Pak1, wherein a compound that enhances autophosphorylation of Pak1 compared to Pak1 autophosphorylation in the absence of the compound is identified as a Pak1 agonist. Such screening techniques are useful in the general identification of a compound that will modulate Pak1 autophosphorylation, with such compounds being useful as therapeutic agents. For example, those compounds that stimulate or increase phosphorylation of Pak1 are useful in the treatment of a cardiac disorder because it is shown herein that enhanced Pak1 autophosphorylation results in the deophosphorylation of cardiac troponin I in cardiomyocytes In another aspect, the invention provides methods of identifying a Pak1 antagonist comprising contacting a candidate compound with purified Pak1, wherein a compound that reduces or inhibits autophosphorylation of Pak1 compared to Pak1 autophosphorylation in the absence of the compound is identified as a Pak1 antagonist. Such screening techniques are useful in the general identification of a compound that will modulate Pak1 autophosphorylation, with such compounds being useful as therapeutic agents. For example, those compounds that inhibit or decrease autophosphorylation of Pak1 are useful in the treatment of disorders with aberrant Pak1 autophosphorylation.

In some embodiments, the Pak1 polypeptide used in the screening methods described here is first purified by affinity chromatography using a decoy Pak1 polypeptide comprising an hemagglutinin (HA) epitope.

In some embodiments, the decoy Pak1 polypeptide comprises a portion of the Pak1 polypeptide, wherein, the decoy Pak1 polypeptide comprises amino acids 131-150 of SEQ ID NO: 1 (YNSKKTSNSQKYMSFTDKSA). In another embodiment, the decoy Pak1 polypeptide comprises amino acids 1-22 of SEQ ID NO: 1 (MSNNGLDIQDKPPAPPM-RNTST). In some embodiments, the Pak1 polypeptide or decoy Pak1 polypeptide is fused to other sequences to make fusion proteins, and/or contain additional moieties such as labels and tags. For example, in one embodiment, the Pak1 polypeptide or portion thereof is linked to a nine amino acid HA epitope (YPYDVPDYA, SEQ ID NO: 2).

In some embodiments, the purified Pak1 polypeptide used in the screening methods described herein comprises a full-length Pak1 polypeptide (amino acids 1-545 of SEQ ID NO: 1; Genbank Accession No. AAC50590. In other embodiments, the purified Pak1 polypeptide comprises a continuous portion of the full-length Pak1 polypeptide that comprises one or more serine/threonine autophosphorylation sites selected from the group consisting of S21, S57, T84, S144, S149, S199, S204, T212, S220, S223, T225, T230 and T423 of SEQ ID NO: 1.

In one aspect, phosphotyrosine levels are measured by standard in vitro techniques well known in the art, such as, and without limitation, enzyme-linked immunosorbant assay (ELISA), radio immunoassay (RIA), Western blot, or immunofluoroescence-based assays. In one aspect, Pak1 activity is measured in biological samples using fluorescent microscopy with fluorescently labeled anti-Pak1 and anti-phosphotyrosine antibodies. Detection is correlated, for example, by a brighter staining signal in a fluorescent microscopy assay, the presence of more staining in a fluorescent microscopy assay, or by decreased fluid levels of phosphorylated Pak1 as detected by Western blot, ELISA, RIA or other immunofluoroescence-based assays, such as fluorescence resonance electron transfer (FRET). It is also contemplated to measure phosphorylated Pak1 using antibodies that specifically recognize Pak1 and which differentiate between a phosphorylated versus unphosphorylated form.

An anti-phosphotyrosine antibody or anti-phosphorylated Pak1 antibody suitable for use in the method of the invention optionally comprisea a label, such as a radioisotope, a fluorophore, a fluorescing protein (e.g., natural or synthetic green fluorescent proteins), a dye, an enzyme, a substrate, or the like. Such labels include, without limitation, biotin molecules, alkaline phosphatase, fluorophores (e.g., fluoroisothiocyanate, phycoerythrin, Texas red, Alexa Fluor stains, and other fluorescent dyes well known in the art), radioisotopes (e.g., $^3$H, Europium$^{3+}$, $^{32}$P), genetically engineered peptide tags such as a histidine (His$_6$) tag linked to the aggregating polypeptide, a myc-tag, a Hemagluttinin (HA) tag, and the like. Biotin, fluorophores, and other contemplated small molecules comprising a label can be linked to the polypeptide by means well-known in the art such as a commercially produced Biotinylation kit (Sigma Chem. Co., St. Louis, Mo.), or alternative methods commonly used in organic chemistry to attach a small molecule to a peptide or protein (see e.g., Current Protocols in Protein Chemistry, John Wiley & Sons, 2001). Genetically engineered tags, e.g., His$_6$ and myc-tags, are operably linked to the polypeptide using standard recombinant DNA methods well known in the art (see e.g., Current Protocols in Molecular Biology, supra), or using conventional peptide synthesis techniques. Such labels facilitate quantitative detection with standard laboratory machinery and techniques.

High-content screens (HCS) provide for analysis of multiple parameters in a single screening assay. For example, in one aspect, autophosphorylation of a Pak1 polypeptide, or a portion thereof, is measured using phosphotyrosine-specific antibodies that fluoresce in a particular excitation channel (e.g., Alexa Fluor 488 excites at 488 nm). Antibodies to additional cell markers which excite at different wavelength ranges (i.e., in different channels) are then added to the same assay.

In one aspect, the candidate compound is a substance capable of modulating (enhancing/stimulating or decreasing/inhibiting) Pak1 autophosphorylation. The candidate compound may be a small molecule, a nucleic acid molecule, a peptide, a polypeptide, an antibody, a synthetic compound, and a naturally-occurring compound. Screening of chemical libraries consisting of both chemically synthesized and natural compounds and combinatorial libraries, are specifically contemplated.

In certain aspects, chemical libraries contain known compounds, proprietary structural analogs of known compounds, or compounds that are identified from natural product screening.

Natural product libraries are collections of materials isolated from natural sources, typically, microorganisms, animals, plants, or marine organisms. Natural products are isolated from their sources by fermentation of microorganisms followed by isolation and extraction of the fermentation broths or by direct extraction from the microorganism or tissue (plant or animal) themselves. Natural product libraries include polyketides, non ribosomal peptides, and variants (including non naturally occurring variants) thereof. See Cane et al., Science, 282:63 68 (1998), incorporated herein by reference.

Combinatorial libraries are composed of large numbers of related compounds, such as peptides, oligonucleotides, or other organic compounds as a mixture. Such compounds are relatively straightforward to design and prepare by traditional automated synthesis protocols, PCR, cloning or proprietary synthetic methods. Of particular interest are peptide and oligonucleotide combinatorial libraries.

Still other libraries of interest include peptide, protein, peptidomimetic, multiparallel synthetic collection, recombinatorial, and polypeptide libraries. For a review of combinatorial chemistry and libraries created thereby, see Myers, Curr. Opin. Biotechnol., 8:701 707 (1997), incorporated herein by reference.

In other aspects, modulators of Pak1 autophosphorylation identified by assessment of the candidate compounds are formulated into compositions which optionally include pharmaceutically acceptable (i.e., sterile and non-toxic) liquid, semisolid, or solid diluents that serve as pharmaceutical vehicles, excipients, or media. Candidate compounds suitable for administration as therapeutics will exhibit acceptable toxicity levels as would be known in the art or determinable by one of skill in the art using routine experimentation.

In some embodiments, compositions comprising one or more modulators of Pak1 autophosphorylation are packaged in forms convenient for delivery. In some embodiments, the compositions are enclosed within a capsule, caplet, sachet, cachet, gelatin, paper, or other container. The dosage units are packaged, e.g., in tablets, capsules, suppositories or cachets.

Antibodies are contemplated as inhibitors of Pak1 autophosphorylation. The term "antibody" is used in the broadest sense and includes fully-assembled antibodies, monoclonal antibodies, polyclonal antibodies, multispecific antibodies (including bispecific antibodies), chimeric antibodies, human antibodies, humanized antibodies, antibody fragments that can bind an antigen (including, Fab', F'(ab)$_2$, Fv, single chain antibodies, diabodies), and recombinant peptides comprising the foregoing as long as they exhibit the desired biological activity. Multimers or aggregates of intact antibodies and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated. Standard techniques are employed to generate polyclonal or monoclonal antibodies directed against Pak1 and to generate useful antigen-binding fragments thereof or variants thereof. Such protocols can be found, for example, in Sambrook et al., Molecular Cloning: a Laboratory Manual. Second Edition, Cold Spring Harbor, N.Y.: Cold Spring Harbor Laboratory (1989); Harlow et al. (Eds), Antibodies A Laboratory Manual; Cold Spring Harbor Laboratory; Cold Spring Harbor, N.Y. (1988). Peptibodies are also contemplated. The term "peptibody" refers to a molecule comprising an antibody Fc domain attached to at least one peptide, which has specific binding properties. The production of peptibodies is generally described in PCT publication WO 00/24782, the disclosure of which is incorporated herein by reference.

In one embodiment, the invention provides in vitro screening methods. In such screening methods, the purified Pak1 or a fragment thereof is either free in solution, fixed to a support, or expressed in or on the surface of a cell. Either the polypeptide or the candidate compound is optionally labeled, thereby permitting determination of binding.

II. Therapeutic Methods

In one embodiment, methods of treating a cardiac disorder in a subject are provided comprising administering to the subject a Pak1 agonist in amount effective to treat the disorder. Exemplary cardiac disorders include, but are not limited to, systolic heart failure, ischemia, arrhythmias, atrial fibrillation, atherosclerosis and angina pectoris.

A "Pak1 agonist" as described herein means a compound capable of enhancing or stimulating Pak1 autophosphorylation. In one embodiment, the Pak1 agonist is a sphingolipid. In another embodiment, the Pak1 agonist is selected from the group consisting of ceramide (including, but not limited to, $C_2$-ceramide and $C_6$-ceramide), safingol, D-sphingosine and sphingosine 1-phosphate, and FTY720 (fingolimod) as well as its derivatives with one or more unsaturated carbon bonds introduced to its hydrophobic side chain. In another embodiment, the Pak1 agonist is a compound identified in the screening methods described herein.

In another embodiment, Pak1 agonists are administered to subject in which treatment with a standard of care therapeutic is contraindicated. For example, methods of treating a cardiac disorder in a subject in which treatment with a β-blocker is contraindicated (i.e., a diabetic subject) are also provided. Such methods comprise administering to the subject a Pak1 agonist in amount effective to treat the disorder. The term "β-blocker" or "beta-blocker" as used herein refers to one or more agents that antagonize the effects of beta-stimulating catecholamines by blocking the catecholamines from binding to the beta-adrenergic receptors. Exemplary beta-blockers include, but are not limited to, acebutolol, alprenolol, atenolol, betantolol, betaxolol, bevantolol, bisoprolol, carterolol, celiprolol, chlorthalidone, esmolol, labetalol, metoprolol, nadolol, penbutolol, pindolol, propranolol, oxprenolol, sotalol, teratolo, timolol and combinations, mixtures and/or salts thereof.

In some embodiments, the method further comprises administering of a standard of care therapeutic (one that is not contraindicated) to the subject. For cardiac disorders, for example, an aspect of the invention is to improve standard of care therapy with co-therapy with one or more of the Pak1 agonists described herein. In some embodiments, the standard of care therapeutic comprises a β-blocker, a statin-related agent (including, but not limited to, lovastatin, atorvastatin, pravastatin, simvastatin and fluvastatin), nicotinic acid, a fibrate (including, but not limited to, bezafibrate, ciprofibrate, clofibrate, gemfibrozil and fenofibrate), bile acid resin(s) (including, but not limited to, cholestyramine, colestipol and cholsevelam), salicylic acid, and a phytosterol (including, but not limited to, stigmastanol, sitosterol, sitostanol and policosanol), In some aspects, the methods are used to treat subjects with a cardiac disorder who do not respond to treatment with standard of care therapeutics. In other aspects, the methods are used to augment treatment with a standard of care therapeutic. Treatment with a Pak1 agonist as described herein in conjunction with a second therapeutic is required in some instances because, e.g., the patient may only partially respond to Pak1 agonist therapy.

In one embodiment, the subject is a mammal, and in other aspects the subject is human. Practice of methods of the invention in other mammalian subjects, especially mammals that are conventionally used as models for demonstrating therapeutic efficacy in humans (e.g., primate, porcine, canine, or rabbit animals), is also contemplated.

In various aspects, the Pak1 agonist and standard of care therapeutic are administered concurrently or sequentially. In embodiments where the Pak1 agonist and standard of care therapeutic are administered separately, one would generally ensure that a significant period of time did not expire between the times of each delivery, such that the Pak1 agonist and standard of care therapeutic(s) would still be able to exert an advantageously combined effect. In such instances, it is contemplated that both modalities would be administered within about 12-24 hours of each other. In some situations, it may be desirable to extend the time period for treatment significantly, from several days (2, 3, 4, 5, 6 or 7) to several weeks (1, 2, 3, 4, 5, 6, 7 or 8). Repeated treatments with one or both agents is specifically contemplated.

III. Pharmaceutical Compositions and Routes of Administration

In some embodiments, the compounds identified in the methods described herein are delivered directly or in pharmaceutical compositions along with suitable carriers or excipients, as is well known in the art. The methods described herein comprise administration of an effective amount of a Pak1 agonist for the treatment of a cardiac disorder. Typical pharmaceutical compositions are formulated to include various components as described in U.S. Pat. No. 7,220,547, the disclosure of which is incorporated by reference for its disclosure of pharmaceutical composition formulations.

An effective amount, e.g., dose, of compound or drug can readily be determined by routine experimentation, as can an effective and convenient route of administration and an appropriate formulation. Various formulations and drug delivery systems are available in the art. (See, e.g., Gennaro, Ed. (2000) Remington's Pharmaceutical Sciences, supra; and Hardman, Limbird, and Gilman, Eds. (2001) The Pharmacological Basis of Therapeutics, supra.)

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art, and include those listed in various pharmacopoeias. (See, e.g., the U.S. Pharmacopeia (USP), Japanese Pharmacopoeia (JP), European Pharmacopoeia (EP), and British pharmacopeia (BP); the U.S. Food and Drug Administration (www.fda.gov) Center for Drug Evaluation and Research (CEDR) publications, e.g., Inactive Ingredient Guide (1996); Ash and Ash, Eds. (2002) Handbook of Pharmaceutical Additives, Synapse Information Resources, Inc., Endicott N.Y.; etc.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Other aspects and advantages of the present invention will be understood upon consideration of the following illustrative examples, which are not intended to be limiting in any way.

EXAMPLES

Example 1

Purification of Pak1 From a Cardiac Sample

Preparation of Muscle Sample. Frozen bovine ventricle muscle (200 g) was cut into small pieces and homogenized in a blender containing 1 liter homogenization buffer (50 mM Tris base, 5 mM EDTA, 2 mM EGTA, 1 mM DTT, 0.5 mM benzamidine, 0.1 mM PMSF, pH 7.2). The homogenized muscle sample was centrifuged at 4500 g for 30 minutes. The supernatant fraction was saved and precipitated with ammonium sulfate (NH4)2SO4 at concentration 25% and 50% (w/v). Precipitates formed by (NH4)2SO4 addition between concentration 25% (w/v) and 50% (w/v) were saved and dialyzed against the homogenization buffer. After dialysis, the sample was filtered and lyophilized. For purification of Pak1 from smaller amounts of sample, the tissues or cells were homogenized in mammalian extraction buffer (50 mM Tris, pH 7.5; 150 mM NaCl; 0.1% Nonide P40; Complete Protease inhibitor cocktail tablets [Roche Diagnostics, cat # 11 873 580 001]). The ratio of tissue:buffer was about 1:5 (v/v). The homogenate was centrifuged in a bench-top centrifuge at 4° C. The supernatant fraction was saved for direct application onto the affinity column.

Peptide Synthesis and the Matrix. The peptides were synthesized in the University of Illinois at Chicago protein core facility. The decoy peptide (YNSKKTSNSQKYMSFT-DKSA-YPYDVPDYA) (SEQ ID NO: 3) contained the Pak1 sequence from amino acids 131-150 linked to a 9 amino acid of HA epitope. The peptide derived from the N-terminal region of Pak1 with the sequence MSNNGLDIQDKPPAPP-MRNTST-YPYDVPDYA (SEQ ID NO: 4) was also used in some purification. The Anti-HA Affinity Matrix (Cat. No. 1 815 016) was purchased from Roche Applied Science (9115 Hague Road, PO Box 50414, Indianapolis, Ind. 46250-0414). The affinity matrix contains antibody specifically bind to HA sequence in protein or peptide.

Affinity Chromatography. The column was first washed with 20 ml equilibration buffer (20 mM Tris, pH 7.5; 0.1 M NaCl; 0.1 mM EDTA). Decoy peptide (3 mg) was applied to the column to saturate the matrix with the peptide. The muscle sample (the lyophilized extract) was dissolved in buffer (20 mM Tris, pH 7.5; 0.1 M NaCl; 0.1 mM EDTA) containing protease inhibitor cocktail tablets. The sample was loaded onto the affinity column and then washed with 20 ml washing buffer (20 mM Tris, pH 7.5; 0.1 M NaCl; 0.1 mM EDTA; 0.05% Tween-20). The Pak1 bound to the gel was eluted with equilibration buffer containing HA peptide (YPYDVPDYA) (SEQ ID NO: 2) at 1 mg/ml. HA peptide was removed from the sample by dialysis in buffer containing 20 mM HEPES, 5 mM NaCl, pH 7.2. The bound Pak1 could also be eluted with 5 ml glycine buffer, pH 2.5 (50 mM glycine-HCl; 0.1% Triton X-100; 0.15 M NaCl).

Data presented in FIG. 2A demonstrate that Pak1 is the major component in the eluted fraction as indicated by the resolution of the samples by SDS-PAGE with Coomassie brilliant blue staining (FIG. 2A, lane 3). Western blotting analysis (FIG. 2B) using an antibody (sc-881) identified the bands shown in FIG. 2A as Pak1. The affinity purification procedure yielded about 200 µg of total protein from the 5 mg muscle protein extract prepared from the frozen ventricle with a yield of 4%. Therefore, the yield of final affinity purification product from the frozen ventricle is about 0.016% (w/w). Pak1 bound to the matrix was eluted with 3 mg of HA peptide that displace the decoy peptide from the matrix. The HA peptide in the eluant was separated from Pak1 protein by use of dialysis tubing permeable to proteins smaller than 12-14 kD (FIG. 1B). The bound Pak1 can also be eluted with Glycine (0.1 M, pH2.0). However, elution with glycine sometimes produces an extra protein bands with molecular weight of 16 kD. Mass spectrometry analysis indicated that the major MS peaks from the digested protein purified matches with Pak1 peptides after trypsin digestion (FIG. 2C).

Example 2

Autophosphorylation of Pak1 by Various Sphingolipids

The following Example demonstrates that various sphingolipids, including $C_2$-ceramide and $C_6$-ceramide) induced autophosphorylation of Pak1.

Figure 1A:
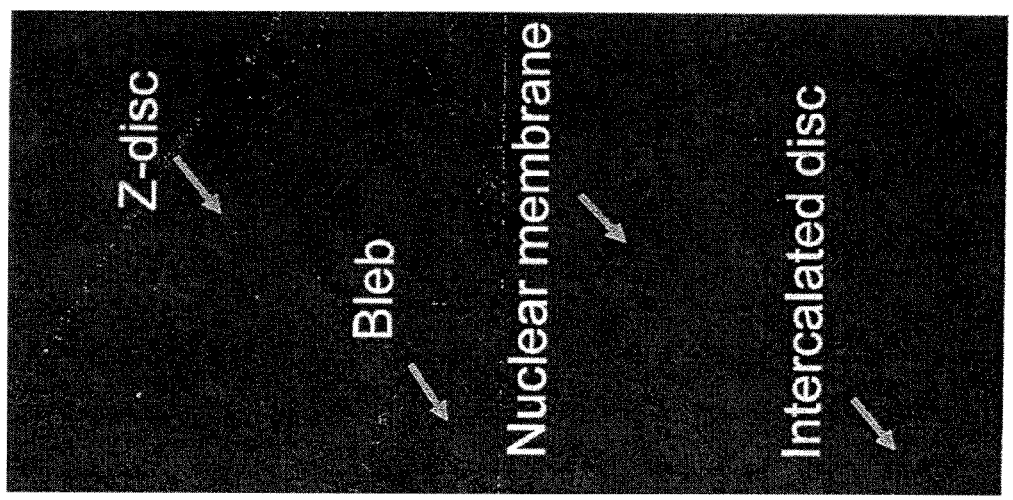
FIG. 1A shows the localization and expression of Pak1 in rat ventricle myocytes detected by immuno-fluorescence and confocal microscopy.

Kinase Assay. Pak1 kinase activity was assayed in the following reaction buffer: 50 mM HEPES, pH 7.3, 10 mM MgCl2, 1 mM DTT, 0.05% Triton X-100) with 10 µCi of [γ32P] ATP (Perkin Elma. [γ-32P]-Adenosine 5'-triphosphate, Specific Activity: 3000 Ci (111TBq)/mmole, 50 mM Tricine (pH 7.6), Concentration: 5 mCi/mL, Catal NEG502H250UC) at 37° C. for 2 h. The kinase reaction was stopped by adding SDS sample buffer followed by boiling for 5 min. In view of reports of sphingosine-1 inducing an increase in Pak1 and Pak2 activity in vitro (Bokoch 1998, p 8137-8144; Roig 2001, p 195-199), the effect of sphingosine and sphingosine-1 phosphate on Pak1 autophosphorylation was also tested (FIG. 3A). The tested agonists (obtained from Calbiochem) included the following: C2 ceramide (N-acetyl-D-erythro-sphingosine), C6 ceramide (N-Hexanoyl-D-erythro-sphingosine) and safingol (Dihydro-L-threo-sphingosine). D-sphingosine (S 6879) and sphingosine 1-phosphate (S 9666) were purchased from Sigma. Sphingosines were dissolved in DMSO. The total reaction volume was 20 µl. DMSO (2 µl) was included in each reaction including the control. Incorporation of 32P from gamma 32P into Pak1 was directly detected by autoradiography after resolve the in vitro reaction products on SDS PAGE. Interestingly, sphingosine-1 phosphate had no significant effect on autophosphorylation of Pak1 at 25 and 50 µM. When the sphingosine phosphate concentration increased to 100 and 200 µM, there was an increase in Pak1 autophosphorylation. In purified Pak1 sample, a 48 kD Pak1 degradation products can sometimes be detected (FIG. 1A, lane 3). When Pak1 activity increased, phosphorylation of the degradation products increased accordingly (FIG. 3).

Results indicated that autophosphorylation of Pak1 purified from cardiac muscle was highly responsive to C2 and C6 ceramide (FIGS. 4A and B). Autophosphorylation of the purified Pak1 increased in the presence of 50 and 100 µM of D-Sphingosine-1 (FIG. 3B), but saphingol (Dihydro-L-threo-Sphingosine) only slightly regulated Pak1 autophosphorylation (FIG. 4C). By gel filtration, the purified Pak1 demonstrated a single major peak. The same experiments were repeated three times each.

Autophosphorylation of Pak1, which correlates with its activity, provided a measure of Pak-1 enzyme function. Initial studies (data not shown) indicated that autophosphorylation of the wt Pak1 was much weaker than the constitutively active Pak1 as shown by others (Manser 1997, p 1129-1143). In all the in vitro assays, we used 4 µg of Pak1 protein. The smaller band (~48 kD) that could be Pak1 degradation products was also phosphorylated. The purified Pak1 also demonstrated kinase activity towards the decoy peptide (YNSKKTSN-SQKYMSFTDKSA) (amino acids 131-150 of SEQ ID NO: 1). The decoy peptide contains Pak1 autophosphorylation sites. The two serine residues that are auto-phosphorylated are situated at the end of the auto-inhibitory sequence. The decoy peptide slightly inhibited autophosphorylation of Pak1. However, it was also phosphorylated and there was a slight increase of the total kinase activity in the presence of the decoy peptide (data not shown).

Discussion:

The purified Pak1 retained low catalytic activity as demonstrated by autophosphorylation in vitro. The constitutively active Pak1 (T423E) has a much higher level of autophosphorylation than the endogenous Pak1 under the same conditions. We found that autophosphorylation of the purified Pak1 is enhanced by D-sphingosine-1, N-acetyle-sphingosine (C2 ceramide) and by hexanoyl-sphingosine (C6 ceramide). This is consistent with an earlier observation that the activities of Pak1 and Pak2 are activated by sphingosine (Bokoch 1998, p 8137-8144; Roig 2001, p 195-199). (11, 12)(18, 19). Our finding that active Pak1 induces dephosphorylation of cTnI and C-protein through activation of PP2A (Ke, 2004, p 194-200) provides a plausible mechanism for induction of protein dephosphorylation by sphingosine. For example, C2-ceramide is a known activator of PP2A (Dobrowsky 1993, p 15523-15530)(13)(20) and may be involved in Bcl2 dephosphorylation (Ruvolo 1999, p 20296-20300). In different types of cells, L-type Ca2+ channel activity was demonstrated to be depressed by C2 ceramide by an unknown mechanism (Chik 1999, p 175-183; Chik 2004, p 5682-5690). C2 ceramide also inhibited proliferation of T-cells stimulated by growth signals (O'Byrne 2000, p 225-230). Moreover, C2 ceramide has preconditioning effects in heart, which has been attributed to generation of reactive oxygen species (Furuya 2001, p 226-232; Lecour 2006, p 1702-1706). (18, 19)(25, 26). Our data indicate that other mechanisms for C2 ceramide involving activation of Pak1 and PP2A need to be considered. To our knowledge, this is the first time demonstration that Pak1 is directly stimulated by C2 and C6 ceramide. The mechanism whereby Pak1 is activated by sphingosine analogs is still not clear. Our studies indicate that C2 and C6 ceramide had stronger effect than sphingosine-1 activating Pak1. Saphingosine only had a small stimulatory effect on Pak1 autophosphorylation. Zenke et al. suggest that sphingosine activates Pak through the P21 binding domain (PBD) (Zenke 1999, p 32565-32573). However, in another study, Cdc42 and sphingosine-1 appears to have a cooperative effect activating the kinase (Chong 2001, p 17347-17353).

Figure 1C:
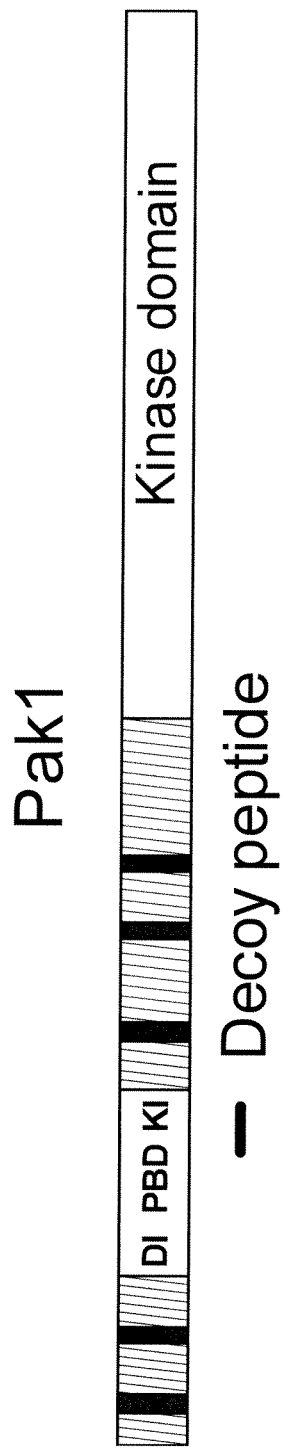
FIG. 1C. The decoy peptide is derived from the autoinhibitory region of Pak1. The autoinhibitory domain of Pak1 is downstream of p21 binding domain (PBD) and by dimerization domain (DI). The vertical bars represent the proline rich sequences in Pak1.
Figure 5A:
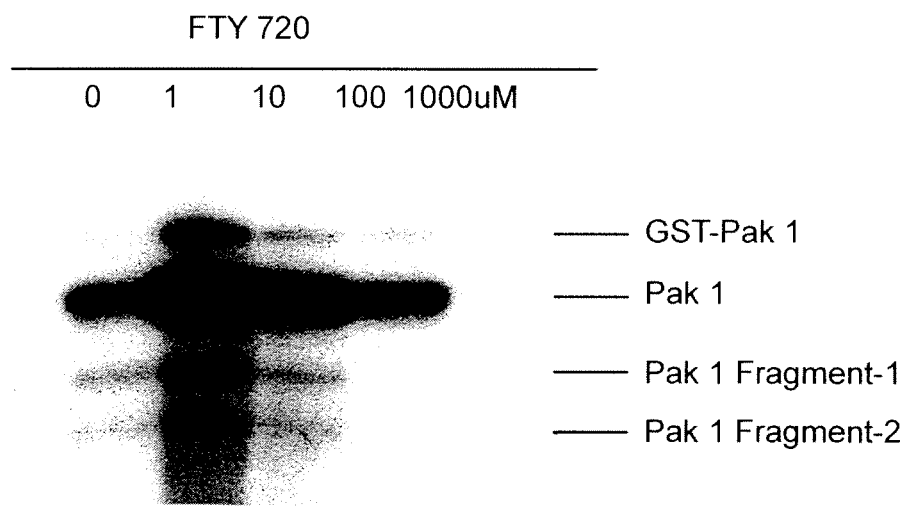
FIGS. 5A and 5B demonstrate that autophosphorylation of Pak1 is stimulated by FTY720.
Figure 5B:
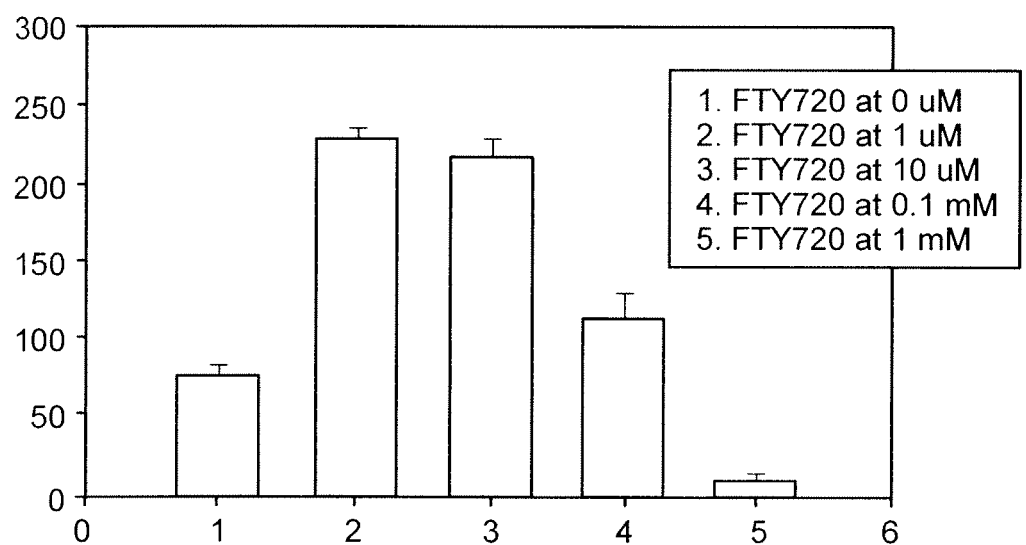

The peptide used to decoy native Pak1 from cardiac muscle is derived from the auto-inhibitory region of Pak1 (Manser 1997, p 1129-1143) (FIG. 1C). The auto-inhibitory region is both downstream of and partially overlaps with the P21 binding domain (PBD) (Zhao 1998, p 2153-2163). A peptide derived from the N-terminal region (the first 21 amino acids of Pak1) that binds to Nck in vitro (Bokoch 1998, p 8137-8144; Zhao 2000, p 3906-3917) also efficiently retained Pak1 in the column (data not shown). The peptide interacts with the catalytic center of the kinase and may regulate the conformation of the catalytic center as demonstrated by NMR studies (Pirruccello 2006, p 312-326). Expression of the peptide plus the P21 binding region produced many cellular changes including inhibition of cell cycle progression (Thullberg 2007, p 1820-1828). The auto-inhibitory region was also deleted in GST-Pak1 which was used for in vitro kinase studies (Polverino 1995, p 26067-26070).

Pak1 is auto-phosphorylated at multiple serine/threonine sites. There are at least six autophosphorylation sites at the N-terminal half of Pak1 (Manser 1997, p 1129-1143). Autophosphorylation at the N-terminus of Pak1 may change its intracellular localization or/and activity (Zhao 2005, p 201-214). It is unclear at which site autophosphorylation occurs first in the activation of Pak1. Furthermore, uncertainty still remains as to whether autophosphorylation is through intermolecular or intra-molecular kinase reactions. Since Pak1 dimer has an anti-parallel conformation, autophosphorylation sites at the N-terminal half of one Pak1 are therefore placed in proximity to the catalytic domain of the other Pak1 (Lei 2000, p 387-397). This suggests that inter-molecular autophosphorylation may occur at the N-terminal autophosphorylation sites.

The purified Pak1 retained low catalytic activity as demonstrated by autophosphorylation in vitro. The constitutively active Pak1 (T423E) has a much higher level of autophosphorylation than the endogenous Pak1 under the same conditions. We found that autophosphorylation of the purified Pak1 is enhanced by D-sphingosine-1, N-acetyle-sphingosine (C2 ceramide) and by hexanoyl-sphingosine (C6 ceramide). This is consistent with an earlier observation that the activities of Pak1 and Pak2 are activated by sphingosine (11, 12)(18, 19). Our finding that active Pak1 induces dephosphorylation of cTnI and C-protein through activation of PP2A (1), provides a plausible mechanism for induction of protein dephosphorylation by sphingosine. For example, C2-ceramide is a known activator of PP2A (13)(20) and may be involved in Bcl2 dephosphorylation (14)(21). In different types of cells, L-type Ca2+ channel activity was demonstrated to be depressed by C2 ceramide by an unknown mechanism (15, 16)(22, 23). C2 ceramide also inhibited proliferation of T-cells stimulated by growth signals (17)(24). Moreover, C2 ceramide has pre-conditioning effects in heart, which has been attributed to generation of reactive oxygen species (18, 19)(25, 26). Our data indicate that other mechanisms for C2 ceramide involving activation of Pak1 and PP2A need to be considered. To our knowledge, this is the first time demonstrating that Pak1 is directly stimulated by C2 and C6 ceramide.

Pak1 contains a few proline-rich sequences at its N-terminus. The proline-rich sequences interact with proteins, such as Nck and Pix. A prominent feature of these proline-rich sequences in Pak1 is that they are followed by autophosphorylation sites. Peptide decoy was first designed to identify proteins that interact with the proline rich sequences in the heart. It turned out Pak1 is the only major protein that binds to the decoy peptides, including the peptide containing 22 amino acids (MSNNGLDIQDKPPAPPMRNTST, amino acids 1-22 of SEQ ID NO: 1) at the N-terminal region of the kinase which contains an autophosphorylation site at Serine 21. Substitution of the serine residue for aspartic acid abolished Nck binding to the peptide in vitro (Zhao 2000, p 3906-3917). In vivo, phosphorylation at the autophosphorylationautophosphorylation sites could be a mechanism to release the "auto-substrate" from the catalytic center of the kinase.

Our understanding of Pak1 function in myocardial cells is still in its infancy, and we think the method reported here is an important step in defining these functions and their mechanisms. Signaling molecules such as Pak1 are often extensively modified by post-translational mechanisms, and in many cases these modifications are associated with pathophysiological conditions. Our method is suitable for study of post-translational modifications of Pak1 in response to different extra-cellular signals and in pathological conditions such as heart failure, arrhythmias and ischemia. The Pak1 kinase purified by this method can also be used for in vitro kinase assay to identify novel activators or inhibitors. Moreover, the method can be adapted for use in purification of Pak isoforms from mammalian tissues other than heart.

Interaction between lipids and a protein kinase may have profound effect on cellular functions (Argraves 2002, p 439-444). The purified Pak1 is stimulated by more than one sphingosine species. It is likely that some other sphiongosine related lipids may also regulate Pak1 activity. Modification of the side chain and the polar groups of sphingosines may produces agonists or antagonists that have even more potent effect on Pak1 autophosphorylation.

Example 3

Autophosphorylation of Pak1 by FTY720

FTY720 (fingolimod) is a drug candidate undergoing clinical trials for organ transplantation and multiple sclerosis. However, the same compound produces cardiac effect (such as a decrease of heart rate) at the same or even a lower dose than that used in the clinical studies intended for organ transplantation and multiple sclerosis. The intracellular target for FTY720 remains controversial.

The kinase assay described above in Example 2 was repeated using FTY720. The results of this assay are set forth below in Table 1.

|  | Sample | | | | |
| --- | --- | --- | --- | --- | --- |
|  | 1 | 2 | 3 | 4 | 5 |
| Kinase buffer | 2 µl | 2 µl | 2 µl | 2 µl | 2 µl |
| Pak1 (0.25 µg) | 5 µl | 5 µl | 5 µl | 5 µl | 5 µl |
| FTY720 (in DMSO) | 0 µM | 1 µM | 10 µM | 100 µM | 1000 µM |
| DMSO | 2 µl | 2 µl | 2 µl | 2 µl | 2 µl |
| 32 P γATP (10 µCi) | 1 µl | 1 µl | 1 µl | 1 µl | 1 µl |
| H$_2$O | 10 µl | 10 µl | 10 µl | 10 µl | 10 µl |

FTY720 is a structural analogue of sphingosine-1 and C2/C6-ceramide. Example 2 demonstrates C2- and C6- ceramides can activate Pak1 activity in vitro and induces dephosphorylation of cardiac troponin cardiomyoctes. We have evidence that FTY720 has the same functional property on Pak1 and in ventricle myocytes. Therefore, like C2- and C6-ceramides, FTY720 can serve as a β-blocker competitor for ischemic heart diseases including angina and systolic heart failure. The anti-(β) adrenergic effect of FTY720 is through activation of Pak1 in the heart. Our current observation further enforced by our previous work on Pak1 function related to heart diseases. Our studies also indicate that even better drug candidates can be designed or screened by testing their effects on Pak1 activation or inhibition using C2/C6 ceramides and FTY720 as prototypes.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

REFERENCES CITED

1. Argraves K M, Obeid L M, and Hannun Y A. Sphingolipids in vascular biology. Adv Exp Med Biol 507: 439-444, 2002.

2. Bagheri-Yarmand R, Mandal M, Taludker A H, et al. Etk/Bmx tyrosine kinase activates Pak1 and regulates tumorigenicity of breast cancer cells. J Biol Chem 276: 29403-29409, 2001.

3. Bokoch G M, Reilly A M, Daniels R H et al. A GTPase-independent mechanism of p21-activated kinase activation. Regulation by sphingosine and other biologically active lipids. J Biol Chem 273: 8137-8144, 1998.

4. Chik C L, Li B, Karpinski E, and Ho A K. Ceramide inhibits L-type calcium channel currents in GH3 cells. Mol Cell Endocrinol 218: 175-183, 2004.

5. Chik C L, Li B, Negishi T et al. Ceramide inhibits L-type calcium channel currents in rat pinealocytes. Endocrinology 140: 5682-5690, 1999.

6. Chong C, Tan L, Lim L, and Manser E. The mechanism of PAK activation. Autophosphorylation events in both regulatory and kinase domains control activity. J Biol Chem 276: 17347-17353, 2001.

7. Dobrowsky R T, Kamibayashi C, Mumby M C et al. Ceramide activates heterotrimeric protein phosphatase 2A. J Biol Chem 268: 15523-15530, 1993.

8. Furuya K, Ginis I, Takeda H et al. Cell permeable exogenous ceramide reduces infarct size in spontaneously hypertensive rats supporting in vitro studies that have implicated ceramide in induction of tolerance to ischemia. J Cereb Blood Flow Metab 21: 226-232, 2001.

9. He H, Hirokawa Y, Gazit A et al. The Tyr-kinase inhibitor AG879, that blocks the ETK-PAK1 interaction, suppresses the RAS-induced PAK1 activation and malignant transformation. Cancer Biol Ther 3: 96-101, 2004.

10. Ke Y, Lei M, Collins T P et al. Regulation of L-type calcium channel and delayed rectifier potassium channel activity by p21-activated kinase-1 in guinea pig sinoatrial node pacemaker cells. Circ Res 100: 1317-1327, 2007.

11. Ke Y, Lum H, and Solaro R J. Inhibition of endothelial barrier dysfunction by P21-activated kinase-1. Can J Physiol Pharmacol 85: 281-288, 2007.

12. Ke Y, Wang L, Pyle W G et al. Intracellular localization and functional effects of P21-activated kinase-1 (Pak1) in cardiac myocytes. Circ Res 94: 194-200, 2004.

13. Lecour S, Owira P, and Opie L H. Ceramide-induced preconditioning involves reactive oxygen species. Life Sci 78: 1702-1706, 2006.

14. Lei M, Lu W, Meng W et al. Structure of PAK1 in an autoinhibited conformation reveals a multistage activation switch. Cell 102: 387-397, 2000.

15. Manser E, Huang H Y, Loo T H et al. Expression of constitutively active alpha-PAK reveals effects of the kinase on actin and focal complexes. Mol Cell Biol 17: 1129-1143, 1997.

16. O'Byrne D and Sansom D. Lack of costimulation by both sphingomyelinase and C2 ceramide in resting human T cells. Immunology 100: 225-230, 2000.

17. Pirruccello M, Sondermann H, Pelton J G et al. A dimeric kinase assembly underlying autophosphorylation in the p21 activated kinases. J Mol Biol 361: 312-326, 2006.

18. Polverino A, Frost J, Yang P et al. Activation of mitogen-activated protein kinase cascades by p21-activated protein kinases in cell-free extracts of Xenopus oocytes. J Biol Chem 270: 26067-26070, 1995.

19. Roig J, Tuazon P T, and Traugh J A. Cdc42-independent activation and translocation of the cytostatic p21-activated protein kinase gamma-PAK by sphingosine. FEBS Lett 507: 195-199, 2001.

20. Ruvolo P P, Deng X, Ito T et al. Ceramide induces Bcl2 dephosphorylation via a mechanism involving mitochondrial PP2A. J Biol Chem 274: 20296-20300, 1999.

21. Sheehan K A, Ke Y, and Solaro R J. p21-Activated kinase-1 and its role in integrated regulation of cardiac contractility. Am J Physiol Regul Integr Comp Physiol 293: R963-973, 2007.

22. Sussman M A, Welch S, Walker A et al. Altered focal adhesion regulation correlates with cardiomyopathy in mice expressing constitutively active rac1. J Clin Invest 105: 875-886, 2000.

23. Thullberg M, Gad A, Beeser A et al. The kinase-inhibitory domain of p21-activated kinase 1 (PAK1) inhibits cell cycle progression independent of PAK1 kinase activity. Oncogene 26: 1820-1828, 2007.

24. Tsakiridis T, Taha C, Grinstein S et al. Insulin activates a p21-activated kinase in muscle cells via phosphatidylinositol 3-kinase. J Biol Chem 271: 19664-19667, 1996.

25. Yang Z, Bagheri-Yarmand R, Wang R A et al. The epidermal growth factor receptor tyrosine kinase inhibitor ZD1839 (Iressa) suppresses c-Src and Pak1 pathways and invasiveness of human cancer cells. Clin Cancer Res 10: 658-667, 2004.

26. Zenke F T, King C C, Bohl B P et al. Identification of a central phosphorylation site in p21-activated kinase regulating autoinhibition and kinase activity. J Biol Chem 274: 32565-32573, 1999.

27. Zhao Z S and Manser E. PAK and other Rho-associated kinases—effectors with surprisingly diverse mechanisms of regulation. Biochem J 386: 201-214, 2005.

28. Zhao Z S, Manser E, Chen X Q et al. A conserved negative regulatory region in alphaPAK: inhibition of PAK kinases reveals their morphological roles downstream of Cdc42 and Rac1. Mol Cell Biol 18: 2153-2163, 1998.

29. Zhao Z S, Manser E, and Lim L. Interaction between PAK and nck: a template for Nck targets and role of PAK autophosphorylation. Mol Cell Biol 20: 3906-3917, 2000.

Shin et a., β-Blocker Pharmacogenetics in Heart Failure, Heart Fail. Rev., 2008.

Latimer et al., Bronchconstriction of the Asthmatic Airway by Inhaled and Ingested Propranolol, Eur. J. Pharmacol., 39:441-445, 1990.

Nagy et al., Bronchial Obstruction Exacerbated furing β Blocker Therapy, Orv. Hetil., 130:2365-2368, 1989.

What is claimed is:

1. A method of treating a cardiac disorder in a subject comprising administering to said subject a p21 activated kinase-1(Pak1) agonist in amount effective to treat said disorder, wherein the Pak1 agonist is fingolimod (FTY720).

2. The method of claim 1, wherein the cardiac disorder is selected from the group consisting of systolic heart failure, ischemia, arrhythmias, atrial fibrillation, atherosclerosis and angina pectoris.

3. The method of claim 1, further comprising administering a standard of care therapeutic to the subject.

4. The method of claim 3, wherein the standard of care therapeutic is selected from the group consisting of β-blockers, nitrates, calcium-channel blockers.

5. The method of claim 3, wherein the Pak 1 agonist and the standard of care therapeutic are administered concurrently.

6. The method of claim 5, wherein the Pak 1 agonist and the standard of care therapeutic are administered in a single formulation.

7. The method of claim 5, wherein the Pak 1 agonist and the standard of care therapeutic are administered as separate formulations.

8. The method of claim 3, wherein the Pak 1 agonist and the standard of care therapeutic are administered sequentially.

9. The method of claim 1, wherein the subject is human.

10. The method of claim 9, wherein the subject is asthmatic.

11. A method of treating a cardiac disorder in a subject in which treatment with a standard of care therapeutic is contraindicated, wherein the method comprises administering to said subject a p21 activated kinase-1(Pak1) agonist in amount effective to treat said disorder, wherein the Pak1 agonist is fingolimod (FTY720).

12. The method of claim 11, wherein the subject is asthmatic.

13. The method of claim 11, wherein the standard of care therapeutic is a β-blocker.

14. The method of claim 11, wherein the cardiac disorder is selected from the group consisting of systolic heart failure, ischemia, arrhythmias, atrial fibrillation, atherosclerosis and angina pectoris.

15. The method of claim 13, further comprising administering a standard of care therapeutic to the subject.

16. The method of claim 15, wherein the standard of care therapeutic is selected from the group consisting of nitrates, calcium-channel blockers.

17. The method of claim 15, wherein the Pak 1 agonist and the standard of care therapeutic are administered concurrently.

18. The method of claim 17, wherein the Pak 1 agonist and the standard of care therapeutic are administered in a single formulation.

19. The method of claim 17, wherein the Pak 1 agonist and the standard of care therapeutic are administered as separate formulations.

20. The method of claim 17, wherein the Pak 1 agonist and the standard of care therapeutic are administered sequentially.

* * * * *

SEQUENCE LISTING

```
<160> NUMBER OF SEQ ID NOS: 4

<210> SEQ ID NO 1
<211> LENGTH: 545
<212> TYPE: PRT
<213> ORGANISM: Homo sapiens

<400> SEQUENCE: 1

Met Ser Asn Asn Gly Leu Asp Ile Gln Asp Lys Pro Pro Ala Pro Pro
1               5                   10                  15

Met Arg Asn Thr Ser Thr Met Ile Gly Ala Gly Ser Lys Asp Ala Gly
            20                  25                  30

Thr Leu Asn His Gly Ser Lys Pro Leu Pro Pro Asn Pro Glu Glu Lys
        35                  40                  45

Lys Lys Lys Asp Arg Phe Tyr Arg Ser Ile Leu Pro Gly Asp Lys Thr
    50                  55                  60

Asn Lys Lys Lys Glu Lys Glu Arg Pro Glu Ile Ser Leu Pro Ser Asp
65                  70                  75                  80
```

-continued

```
Phe Glu His Thr Ile His Val Gly Phe Asp Ala Val Thr Gly Glu Phe
                 85                  90                  95
Thr Gly Met Pro Glu Gln Trp Ala Arg Leu Leu Gln Thr Ser Asn Ile
            100                 105                 110
Thr Lys Ser Glu Gln Lys Lys Asn Pro Gln Ala Val Leu Asp Val Leu
        115                 120                 125
Glu Phe Tyr Asn Ser Lys Lys Thr Ser Asn Ser Gln Lys Tyr Met Ser
    130                 135                 140
Phe Thr Asp Lys Ser Ala Glu Asp Tyr Asn Ser Ser Asn Ala Leu Asn
145                 150                 155                 160
Val Lys Ala Val Ser Glu Thr Pro Ala Val Pro Val Ser Glu Asp
                165                 170                 175
Glu Asp Asp Asp Asp Asp Ala Thr Pro Pro Val Ile Ala Pro
            180                 185                 190
Arg Pro Glu His Thr Lys Ser Val Tyr Thr Arg Ser Val Ile Glu Pro
        195                 200                 205
Leu Pro Val Thr Pro Thr Arg Asp Val Ala Thr Ser Pro Ile Ser Pro
    210                 215                 220
Thr Glu Asn Asn Thr Thr Pro Pro Asp Ala Leu Thr Leu Asn Thr Glu
225                 230                 235                 240
Lys Gln Lys Lys Pro Lys Met Ser Asp Glu Glu Ile Leu Glu Lys
                245                 250                 255
Leu Arg Ser Ile Val Ser Val Gly Asp Pro Lys Lys Tyr Thr Arg
            260                 265                 270
Phe Glu Lys Ile Gly Gln Gly Ala Ser Gly Thr Val Tyr Thr Ala Met
        275                 280                 285
Asp Val Ala Thr Gly Gln Glu Val Ala Ile Lys Gln Met Asn Leu Gln
    290                 295                 300
Gln Gln Pro Lys Lys Glu Leu Ile Ile Asn Glu Ile Leu Val Met Arg
305                 310                 315                 320
Glu Asn Lys Asn Pro Asn Ile Val Asn Tyr Leu Asp Ser Tyr Leu Val
                325                 330                 335
Gly Asp Glu Leu Trp Val Val Met Glu Tyr Leu Ala Gly Gly Ser Leu
            340                 345                 350
Thr Asp Val Val Thr Glu Thr Cys Met Asp Glu Gly Gln Ile Ala Ala
        355                 360                 365
Val Cys Arg Glu Cys Leu Gln Ala Leu Glu Ser Leu His Ser Asn Gln
    370                 375                 380
Val Ile His Arg Asp Ile Lys Ser Asp Asn Ile Leu Leu Gly Met Asp
385                 390                 395                 400
Gly Ser Val Lys Leu Thr Asp Phe Gly Phe Cys Ala Gln Ile Thr Pro
                405                 410                 415
Glu Gln Ser Lys Arg Ser Thr Met Val Gly Thr Pro Tyr Trp Met Ala
            420                 425                 430
Pro Glu Val Val Thr Arg Lys Ala Tyr Gly Pro Lys Val Asp Ile Trp
        435                 440                 445
Ser Leu Gly Ile Met Ala Ile Glu Met Ile Glu Gly Glu Pro Pro Tyr
    450                 455                 460
Leu Asn Glu Asn Pro Leu Arg Ala Leu Tyr Leu Ile Ala Thr Asn Gly
465                 470                 475                 480
Thr Pro Glu Leu Gln Asn Pro Glu Lys Leu Ser Ala Ile Phe Arg Asp
                485                 490                 495
Phe Leu Asn Arg Cys Leu Glu Met Asp Val Glu Lys Arg Gly Ser Ala
            500                 505                 510
```

```
Lys Glu Leu Leu Gln His Gln Phe Leu Lys Ile Ala Lys Pro Leu Ser
        515                 520                 525
Ser Leu Thr Pro Leu Ile Ala Ala Ala Lys Glu Ala Thr Lys Asn Asn
    530                 535                 540
His
545

<210> SEQ ID NO 2
<211> LENGTH: 9
<212> TYPE: PRT
<213> ORGANISM: Homo sapiens

<400> SEQUENCE: 2

Tyr Pro Tyr Asp Val Pro Asp Tyr Ala
1               5

<210> SEQ ID NO 3
<211> LENGTH: 29
<212> TYPE: PRT
<213> ORGANISM: Homo sapiens

<400> SEQUENCE: 3

Tyr Asn Ser Lys Lys Thr Ser Asn Ser Gln Lys Tyr Met Ser Phe Thr
1               5                   10                  15
Asp Lys Ser Ala Tyr Pro Tyr Asp Val Pro Asp Tyr Ala
            20                  25

<210> SEQ ID NO 4
<211> LENGTH: 31
<212> TYPE: PRT
<213> ORGANISM: Homo sapiens

<400> SEQUENCE: 4

Met Ser Asn Asn Gly Leu Asp Ile Gln Asp Lys Pro Pro Ala Pro Pro
1               5                   10                  15
Met Arg Asn Thr Ser Thr Tyr Pro Tyr Asp Val Pro Asp Tyr Ala
            20                  25                  30
```